Figure 1:
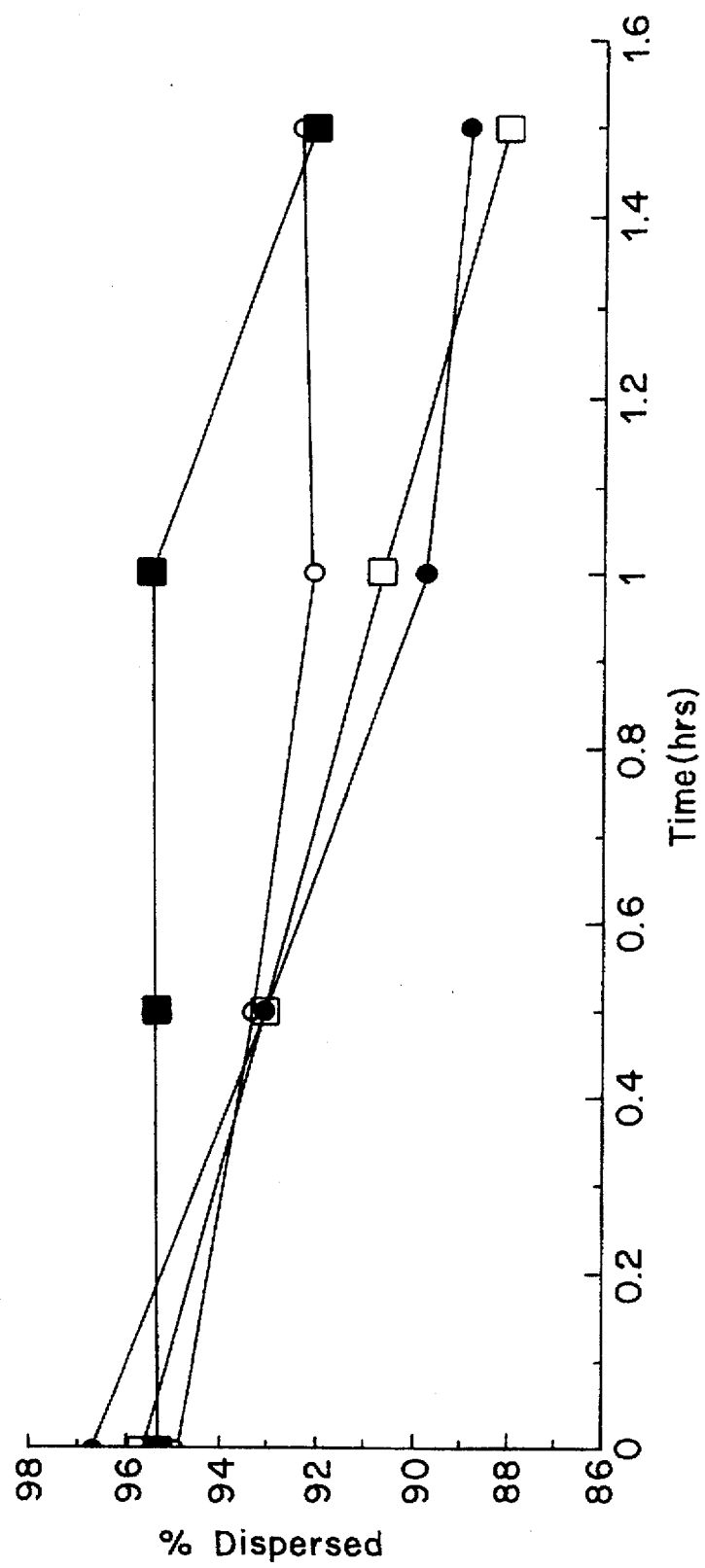

United States Patent [19]
Narayanan

[11] Patent Number: 5,734,006
[45] Date of Patent: *Mar. 31, 1998

[54] N-VINYL LACTAM COPOLYMER CONTAINING TABLETS OF LOW FRIABILITY AND HIGH RATE OF DISSOLUTION

[75] Inventor: Kolazi S. Narayanan, Wayne, N.J.

[73] Assignee: ISP Investments Inc., Wilmington, Del.

[*] Notice: The term of this patent shall not extend beyond the expiration date of Pat. No. 5,555,089.

[21] Appl. No.: 698,141

[22] Filed: Aug. 15, 1996

Related U.S. Application Data

[63] Continuation-in-part of Ser. No. 349,774, Dec. 6, 1994.
[51] Int. Cl.$^6$ .................................................. C08G 69/14
[52] U.S. Cl. ................ 528/323; 528/310; 528/326; 528/363; 424/470; 424/482; 424/489; 424/501
[58] Field of Search ...................................... 424/470, 482, 424/489, 501; 528/326, 310, 363, 323

[56] References Cited

U.S. PATENT DOCUMENTS

| | | | |
|---|---|---|---|
| 5,137,730 | 8/1992 | Dennis et al. | 424/470 |
| 5,200,193 | 4/1993 | Radebaugh et al. | 424/470 |
| 5,242,684 | 9/1993 | Merianos | 424/501 |
| 5,326,572 | 7/1994 | Mehra et al. | 424/470 |
| 5,354,560 | 10/1994 | Lovrecich | 424/501 |
| 5,405,412 | 4/1995 | Willey et al. | 8/111 |

FOREIGN PATENT DOCUMENTS

0649649A2   4/1995   European Pat. Off. .

Primary Examiner—P. Hampton-Hightower
Attorney, Agent, or Firm—Marilyn J. Maue; Walter Katz; Joshua J. Ward

[57] ABSTRACT

This invention relates to a coprecipitated binder composition used for the compression of pharmaceutically and agriculturally active components to provide a non-friable pill or tablet of increased hardness with remarkably improved rate of dissolution and improved stability in aqueous solution. The invention also relates to the process for preparing the binder and to its incorporation in a formulation with the active ingredient.

11 Claims, 2 Drawing Sheets

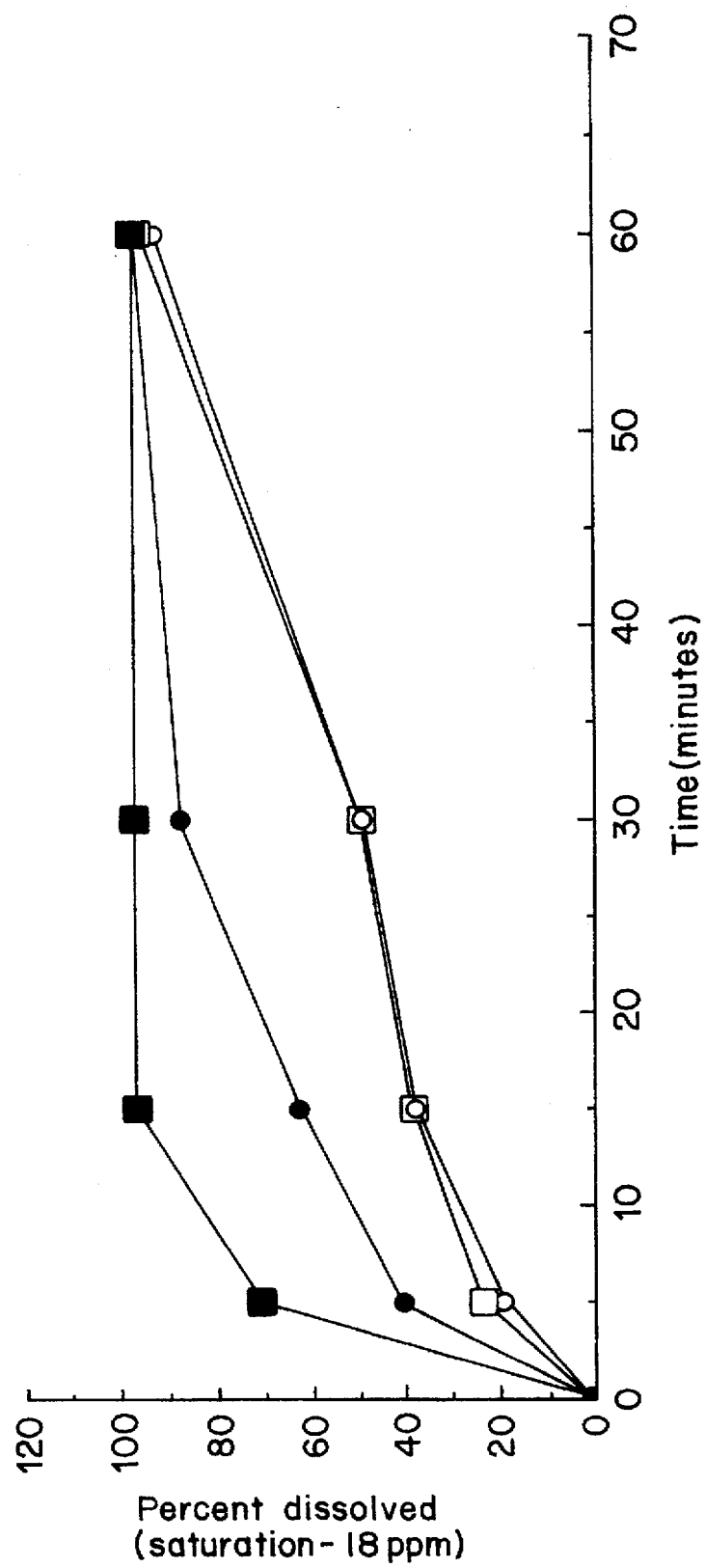

N-VINYL LACTAM COPOLYMER CONTAINING TABLETS OF LOW FRIABILITY AND HIGH RATE OF DISSOLUTION

This application is a continuation-in-part of Ser. No. 08/349,774, filed Dec. 6, 1994.

DISCUSSION OF THE PRIOR ART

Pharmaceutical and agricultural compositions containing polymeric lactam carriers or binders have been found wanting in several respects. Either they have exhibited undesirable friable properties when subjected to high compression, thus causing difficulties in packaging and shipping as well as increasing costs due to losses of uniform tablet size with accompanying inaccuracy in prescribed dosage levels or else the compositions are characterized as having a low rate of dissolution which seems to vary directly with the degree of compression since the forces imposed during manufacture compresses the lattice structure thus causing poor liquid penetration. Undesirable rates of dissolution have been particularly recognized where vinyl lactam polymers are employed as binders in the agrichemical and pharmaceutical compositions.

Accordingly, it is an object of the present invention to provide a binder for use in pharmaceutical and agricultural chemical formulations which markedly increases the rate of tablet dissolution while retaining a high lattice energy matrix resistant to crumbling or powdering during the packaging process.

Another object of the invention is to provide a binder material which reduces the number of components needed in the production of readily dissolvable pills and tablets.

Still another object is to facilitate the manufacture of tablets having the above improved properties by a simple and economical process.

These and other objects of the invention will become apparent from the following description and disclosure.

THE INVENTION

In accordance with the present invention there is provided a composition containing a medically or agriculturally prescribed amount of an active chemical and a binder comprising a copolymer of an N-vinyl lactam containing from 4 to 6 ring carbon atoms and an organic polybasic carboxylic acid combined in a mole ratio of polymer to —COOH group of between about 1:0.1 and about 1:10, preferably between about 1:0.5 and about 1:4.

The N-vinyl lactam polymers of the invention include copolymers with one or more comonomer selected from the group including a vinyl ester, such as for example vinyl acetate, vinyl ethylate, a $C_1$ to $C_4$ alkyl-acrylate or methacrylate; a $C_3$ to $C_{12}$ alpha-olefin, such as for example 2-propene, 3-butene, 7-octene, 9-decene, 11-dodecene; an N-vinyl amide, such as for example N-vinyl succinamide, N-vinyl adipamide and an N-vinyl imide such as N-vinyl succinimide. The N-vinyl lactam monomer can be unsubstituted or substituted on a ring carbon atom with a $C_1$ to $C_4$ alkyl group. Such lactam monomers are exemplified by N-vinyl pyrrolidone, N-vinyl caprolactam, 3-methyl N-vinyl pyrrolidone, 3,4-dimethyl N-vinyl pyrrolidone, ethyl N-vinyl caprolactam, 3-butyl N-vinyl pyrrolidone etc. and can be used as lactam mixtures, such as for example a mixture of N-vinyl pyrrolidone and N-vinyl caprolactam with said comonomer. For the purposes of this invention, the unsubstituted lactam monomers are preferred and N-vinyl pyrrolidone or mixtures of N-vinyl pyrrolidone and N-vinyl caprolactam are most preferred. The vinyl esters are the preferred comonomers of this invention. In general, the copolymers of the present invention contain from about 40 to 60 wt. % N-vinyl lactam monomer and are water soluble or water dispersible polymers having a number average molecular weight between about 2,500 and about 1,000,000. However, these copolymers when blended with an active biochemical, in their compressed form, are subject to crumbling or powdering due to attrition when packaged in bundles.

Suitable polybasic acids of the invention are polycarboxylic acids containing from 3 to 14 carbon atoms, which are unsubstituted or optionally substituted with hydroxy. These acids are defined by the formula

$$(HO)_x-R-(COOH)_y$$

wherein x has a value of from 0 to 4, y has a value of from 2 to 4 and R is alkylene having 1 to 10 carbon atoms. The preferred acids of this invention are the di- and tri-carboxylic acids containing from 3 to 6 carbon atoms as in adipic, citric, glutaric, malonic, malic, maleic, succinic, saccharic, saccharonic, tartaric, tricarballylic acids and the like.

The acid is coprecipitated with the polymer component forming a copolymeric, hydrogen bondable complex. This condition retains the high lattice packing capability of the copolymer under high compression while providing hydrogen bondable sites for minimizing friability and surprisingly, at the same time, maximizing dissolution rate. The preferred vinyl ester comonomer maximizes the solution through free carboxyl groups of the comonomer to provide a formed pill or tablet suitable for packaging and readily dissolvable in water, enzymic fluid or other liquids by the consumer. Normally one would expect that the harder product resulting from the use of a binder having high lattice packing would hinder rapid dissolution of the active component in an aqueous system. However, surprisingly the product of this invention possesses a markedly increased rate of dissolution. The present composition also eliminates or minimizes the need for extraneous components such as surfactants, emulsifying agents, solubilizers and the like; although a buffering agent, such as an alkali metal salt or an ammonium or alkyl ammonium salt of the present acid, in an amount up to about 30 wt % of the total composition, is optionally included to maintain a pH of 5–7 in cases where acidity may cause a problem. For example a buffering agent may be employed to neutralize acidity or the action of stomach acids in medicinal use applications. Other suitable buffering agents include the alkali metal, ammonium and alkyl ammonium salts of phosphoric acid. Also, if desired, the composition may contain a nonionic or anionic surfactant or a mixture thereof in an amount sufficient to achieve a specific affect.

The present solids composition also contains a conventionally prescribed amount of an active ingredient, e.g. an agrichemical or pharmaceutical component, which is insoluble or difficultly soluble in water or which possesses such high water solubility that rainfastness properties are minimal. In the later case, the film forming capability of the polymer upon dissolution, enhances retention of the active component on the site of application.

The active ingredient usually does not exceed 85 wt % of the total solids in the composition and includes a pesticide, fungicide, herbicide, plant growth regulant, nematocide, fertilizer, nutrient, bactericide, virucide or any of the drugs useful for treating pathogens, relaxant, antiacid, pain blocker, or any medication which can be administered in solid, prescribed dosage form. Mixtures of these active chemicals may also be employed in the compositions of the present invention.

The present solid compositions are economically prepared by dissolving the copolymer and the acid in a mutual solvent, e.g. water, a $C_1$ to $C_4$ alcohol, glycerol, glycols or aqueous solutions of said solvents; forming the complex by coprecipitation of the components at a moderate temperature, e.g. from about 35° C. to about 60° C., under continuous agitation over a period of from about 2 to about 8 hours followed by distillation under vacuum at below 60° C., preferably at 40°–55° C., to remove solvent and form the crystalline binder product. Alternatively, when water is employed as the solvent, it can be removed by freeze drying. The binder product is then dried and ground to an average diameter particle size below 200 mesh before mixing with a prescribed amount of the active chemical in solid form. The resulting mixture is then compressed into pills or tablets according to conventional procedures.

Alternatively, an aqueous mixture of the copolymer/acid complex can be sprayed onto a preformed pharmaceutical or agricultural chemical formulation in a fluid bed mixing process preceding tabulation or granulation. The dissolution rate of the resulting tablets is increased 3 to 10 fold per 1% over tablets formed from other non-complexed polymeric N-vinyl lactams or their mixtures with other dissolution promoting agents.

The improved stability of aqueous dispersions employing the present active/binder compositions over those previously employed is unexpected in view of the increased hardness of the compressed product. FIG. 1 compares the amount of water insoluble active component retained in dispersion as a function of time, when 1 g of the active-binder composition is stirred and dispersed in 100 ml deionized water over a period of 2 hours. The various active/binder compositions are indicated by symbols according to the following

| Symbol | Active/Binder Composition* |
| --- | --- |
| o | 90% PVP + 10% active (cypermethrin) |
| ● | 48% PVP + 42% citric acid + 10% active (cypermethrin) |
| □ | 90% VP/Va + 10% active (cypermethrin) |
| ■ | 46% VP/VA + 44% citric acid + 10% active (cypermethrin) |

*The active/binder compositions were prepared by charging cypermethrin in a 500 ml round bottom flask together with copolymer acid and ethanol solvent. The charge was kept at about 50° C. for a period of 4 hours. The solvent was then evaporated at reduced pressure and the granules that remained were scraped from the flask for testing.

The extended duration and high load of active remaining in dispersion with the present copolymer/acid binder, i.e. 96% active in dispersion for at least 1 hour, as compared with only 89% active in dispersion using polyvinyl pyrrolidone/acid binder illustrates a significant improvement in stability of this invention using the copolymer complex.

FIG. 2 illustrates the dissolution rate of 2.5 grams active in 1 liter of water from granules having the above compositions and indicated by the same symbols. This figure indicates the time required to form a saturated aqueous solution of the active component, i.e. cypermethrin. As shown, a saturated solution was reached after only 15 minutes mechanical stirring with active in VP/VA/acid complex binder; whereas the desired saturated solution was achieved only after about 60 minutes mechanical stirring with active in PVP/acid complex binder. The faster dissolution rate of the present compositions provides more rapid and complete response on the subject undergoing treatment.

Because esters are incapable of hydrogen bonding, the vinyl ester comonomer in the present compositions makes available free —COOH groups derived from the polybasic acid. These acid groups act as a wick through capillary action for water in aqueous spray applications.

Having generally described the invention, reference is now had to the following examples which illustrate preferred embodiments and provide comparative data; however, these examples are not to be construed as limiting to the scope of the invention as more broadly defined above and in the appended claims.

EXAMPLE 1

A 5-liter round bottom flask was charged with 32.7 g Agrimer 30*, 28.25 g citric acid and 550 g anhydrous ethanol. The contents were heated at 60° C. under nitrogen and stirred with a magnetic stirrer for a period of 4 hours. The resulting solution (about 550 cc) was introduced into a rotary evaporator where ethanol was removed under reduced pressure at less than 60° C. The solid material obtained was ground to 150–250 microns. The total solid recovered for testing was 60 g. The sample was analyzed for its homogeneity and found to contain 46±0.5% citric acid. The number of inversions needed to dissolve 1% polymer, (i.e. about 2% complex) was found to be 45.

*Polyvinyl pyrrolidone K 30 (PVP)

When this example was repeated in the absence of citric acid using 32.7 g PVP dissolved in 550 ml ethanol the resulting dried product required more than 90 inversions to dissolve 1% of polymer.

EXAMPLE 2

A 1-liter round bottom flask was charged with 31.3 g vinyl pyrrolidone/vinyl acetate copolymer (Agrimer VA 6—PVP VA 630), 29.7 g anhydrous citric acid and 550 g ethanol. The charge was heated under a stream of nitrogen at about 60° C. for a period of 4 hours. The ethanol was removed by a rotary evaporator under reduced pressure, so that the temperature was below 60° C. The solid that was separated was ground in a dry blender to 150–250 micron size. The number of inversions needed to dissolve 1% copolymer (i.e. about 2% complex) was 9.7±1.5.

When this example was repeated in the absence of citric acid, the dried product required more than 120 inversions to dissolve 1% polymer.

This example is repeated, except that N-vinyl pyrrolidone/N-vinyl succinamide is substituted for the VA/VP copolymer. The resulting binder composition requires fewer inversions to dissolve polymer than that reported in Example 1. Further, this copolymer composition has a dispersion stability similar to that using VP/VA. The improvement observed with the vinyl lactam copolymers over the vinyl lactam homopolymers is attributed to their hydrophobicity which minimizes absorption of water and provides an extended storage period for tablets employing these binders.

EXAMPLE 3

3A

Example 2 was repeated using 31.95 g vinyl pyrrolidone/butene-1 copolymer (Agrimer AL 10—Ganex P 904) in the place of Agrimer VA 6, 29.7 g anhydrous citric acid and 550 g ethanol. The charge was heated under a stream of nitrogen at about 60° C. for a period of 4 hours. The ethanol was removed by a rotary evaporator under reduced pressure, at a temperature below 60° C. The recovered solid was ground in a dry blender and similarly separated into three portions, i.e. 200 mesh (150–250 microns), 200 mesh (75–150 microns), and <200 mesh (<75 microns), using U.S. standard sieves.

3B

A 31.95 g sample of the polymer vinyl pyrrolidone/butene-1 copolymer (Agrimer AL 10—Ganex P 904) was prepared as above, except that citric acid was omitted. This sample was similarly separated into three particle size groups, i.e. 100 mesh (150–250 microns), 200 mesh (75–150 microns) and <200 mesh (<75 microns) via sieving as above. The dissolution rates are shown below in Table I.

3C

When example 3A was repeated in the absence of citric acid, the product required between 122 and 202 inversions to dissolve 1% copolymer in deionized water.

TABLE I

| Ex. | Particle Size | Average No. of Inversions |
|---|---|---|
| 3A | 150–250 microns | 75 ± 8 |
| 3A | 75–150 microns | 98 ± 7 |
| 3A | <75 microns | 100 ± 6.0 |
| 3B | 150–250 microns | >180 |
| 3B | 75–150 microns | >180 |
| 3B | <75 microns | >200 |

EXAMPLE 4

4A

In a 2-liter Hobart mixer, 100 g commercial Assert bisulfate was charged with 5 g Agrimer K 30 (PVP K 30). While the charge was thoroughly mixed in the dry state for a period of 1 hour, 5–7 ml deionized water was added over a period of 7–8 minutes, and agitation was continued for additional 30 minutes. The sample was dried in an electric oven for a period of 16 hours to produce a residual moisture content of 1%. The granules produced were evaluated for hardness.

4B

Part 4A was repeated except that in the place of 5 g Agrimer K 30, 9.8 g of the coprecipitate of Example 2 was used. The resulting granules were compared with those of Example 4A. The granules of this example were harder.

EXAMPLE 5

The granules from Example 2 were loaded in a Tablet press with an average charge of 50 mg per tablet and tablets were produced at a compression pressure of 100 kg.

EXAMPLE 6

The granules from Example 4B were similarly loaded in a Tablet press with an average charge of 50 mg per tablet and tablets were produced at a compression pressure of 120 kg.

It was found that the tablets of this example were less friable, harder, and dissolved faster than those of Example 4A.

The substitution of any of the foregoing organic polybasic acids for citric acid in the above examples provides similar results. Although the optimum mole ratio of polymer to di-, tri- and tetra- carboxylic acids is indicated above, the ratio selected can depend on the option of the formulator as needs of application demand. Hence, where a dicarboxylic compound is selected and the ultimate use, e.g. an agricultural product, does not demand the highest degree of attrition resistance, or a somewhat more rapid dissolution rate is not prohibitive, a mole ratio of copolymer to acid within the lower portion of the above range may be selected.

What is claimed is:

1. An attrition resistant compressed solid composition having a dissolution or dispersion rate less than 100 inversions/500 mg of composition and comprising a chemically effective amount of an agrichemical or pharmaceutical component in solid form and a binder consisting essentially of an N-vinyl lactam copolymer/polybasic carboxylic acid complex combined in a mole ratio of copolymer to carboxyl group of between about 1:0.1 and about 1:10; said polybasic carboxylic acid having the formula

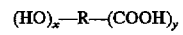

$$(HO)_x\text{—R—}(COOH)_y$$

wherein x has a value of from 0 to 4; y has a value of from 2 to 4 and R is alkylene of 1 to 10 carbon atoms.

2. The composition of claim 1 wherein the mole ratio of polymer to carboxyl group is between about 1:0.5 and about 1:4.

3. The composition of claim 1 which additionally contains up to about 30 wt %, based on complex, of an alkali metal salt, an ammonium salt or a lower alkyl ammonium salt of a polybasic carboxylic acid as a buffering agent.

4. The composition of claim 1 wherein said N-vinyl lactam monomer of the copolymer is selected from the group consisting of the polymer of N-vinyl pyrrolidone, N-vinyl caprolactam and mixtures thereof.

5. The composition of claim 1 wherein said N-vinyl lactam copolymer is selected from the group consisting of N-vinyl pyrrolidone and/or N-vinyl caprolactam monomer with a comonomer selected from the group consisting of a vinyl ester, an N-vinyl amide, an N-vinyl imide and an α-olefin.

6. The composition of claim 5 wherein said N-vinyl lactam is N-vinyl pyrrolidone.

7. The composition of claim 6 wherein said comonomer is vinyl acetate.

8. The composition of claim 1 wherein said polybasic carboxylic acid is a di- or tri- basic carboxylic acid.

9. The composition of claim 8 wherein said tricarboxylic acid is citric acid.

10. The composition of claim 1 which additionally contains a buffering agent selected from the group consisting of an alkali metal salt, an ammonium salt and an alkyl ammonium salt of phosphoric acid and mixtures thereof.

11. The composition of claim 1 additionally containing a non-ionic and/or anionic surfactants.

* * * * *